United States Patent [19]

Nagano et al.

[11] Patent Number: 4,545,942
[45] Date of Patent: Oct. 8, 1985

[54] AMINO-ACID DERIVATIVES, THEIR PREPARATION AND THEIR USE AS PHARMACEUTICALS

[75] Inventors: Mitsuo Nagano; Koichi Hirai; Kouichi Kitamura; Kenkichi Shinkai; Hiroshi Yasuda, all of Hiromachi, Japan

[73] Assignee: Sankyo Company, Limited, Tokyo, Japan

[21] Appl. No.: 597,817

[22] Filed: Apr. 9, 1984

Related U.S. Application Data

[63] Continuation of Ser. No. 244,802, Mar. 17, 1981, abandoned.

[30] Foreign Application Priority Data

Mar. 22, 1980 [JP] Japan .................. 55-36562

[51] Int. Cl.[4] .............. C07C 121/78; A61K 31/275
[52] U.S. Cl. .................. 260/465 D; 514/521
[58] Field of Search ............ 260/465 D; 424/304

[56] References Cited

U.S. PATENT DOCUMENTS 2,847,451  8/1958  Schott et al. ............... 424/304 X
2,891,053  6/1959  Meyer et al. ............... 424/304 X
3,125,583  3/1964  Leonard .................... 260/465 D X

OTHER PUBLICATIONS

Knobler, et al., J. Chem. Soc., C., 14, pp. 1821–1824, (1969).
Wakamatsu, et al., J. Chem. Soc., D., Chem. Commun., 23, p. 1540, (1971).
Pichat, et al., Bull. Soc. Chim., Fr., (1970), 5, pp. 1837–1838.
Umezawa, et al., J. Antibiotics, 29(8), pp. 857–859, (1976).
Kobayashi, et al., Synthesis and Immunological Activities of Muramyl Dipeptide Derivatives, 7th Symposium on Progress in Organic Reactions and Synthesis; Gifu, Japan, (1980).
Wegman, et al., C.A., 95, 169043p, (1981).

*Primary Examiner*—Joseph Paul Brust
*Attorney, Agent, or Firm*—Frishauf, Holtz, Goodman & Woodward

[57] ABSTRACT

New compounds useful as immunoregulatory and antineoplastic agents are amino-acid derivatives of formula:

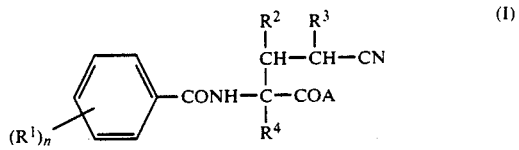

wherein:
n is an integer from 1 to 5;
$R^1$ is a hydrogen atom, an alkyl group, a haloalkyl group, a halogen atom, a mercapto group, an alkylmercapto group, a hydroxy group, an alkoxy group, an acyloxy group, a carboxyl group, an alkoxycarbonyl group, an amino group, an alkyl-substituted amino group, an aryl-substituted amino group, an acylamino group, a haloalkoxycarbonylamino group, an alkanesulphonyl group, a nitro group or a cyano group (and, when n is an integer from 2 to 5, the radicals $R^1$ may be the same or different);
$R^2$ and $R^3$ may be the same or different and each is a hydrogen atom or an alkyl group;
$R^4$ is a hydrogen atom, an alkyl group, a cyano group, a cyanoalkyl group, a hydroxyalkyl group, an alkoxycarbonyl group, a carboxyl group, an aryl group, an aralkyl group, a mercaptoalkyl group, an alkylthioalkyl group, or a thioalkyl group (the free bond of the sulphur in said thioalkyl group being joined to the sulphur of another moiety of the same formula); and
A is a hydroxy group, an alkoxy group, an amino group, an alkyl-substituted amino group (optionally halogen- or carbamoyl- substituted in the alkyl moiety), a hydrazino group, an alkyl- or aryl- substituted hydrazino group, a hydroxylamino group, an alkoxyamino group or an aralkyloxyamino group;
and the pharmaceutically acceptable salts thereof.

16 Claims, No Drawings

AMINO-ACID DERIVATIVES, THEIR PREPARATION AND THEIR USE AS PHARMACEUTICALS

This application is a continuation of application Ser. No. 244,802, filed Mar. 17, 1981 (abandoned).

BACKGROUND TO THE INVENTION

The present invention relates to novel amino-acid derivatives, to their use as pharmaceuticals, and to their preparation. More particularly, the compounds of the invention are 2-cyanoethyl-substituted N-benzoylaminoalkanoic acid derivatives which possess immunoregulatory and anti-tumor activities.

In the literature, Knobler Y. et al., J. Chem. Soc. C. (14) 1821–4 (1969), discloses N-(substituted benzoyl) glutamic acid derivatives which have a 2-carboxyethyl substituent in place of the 2-cyanoethyl substituent of the compounds of the present invention; Wakamatsu H. et al., J. Chem. Soc. D. Chem. Commun., (23) 1540 (1971), discloses the compound 2-(2-cyanoethyl)-N-acetylglycine; and Pichat L. et al., Bull. Soc. Chim. Fr. 1970(5) 1837–8, discloses, as an intermediate for amino acid synthesis, the compound 2-(3-cyanopropyl)-N-benzoylglycine. However, no immunoregulatory or anti-tumor activity is disclosed for any of these compounds. On the other hand, Umezawa H. et al., J. Antibiotics 29(8), 857–859 (1976), discloses the compound "bestatin", which is [(2S, 3R)-3-amino-2-hydroxy-4-phenylbutanoyl]-L-leucine, which is said to exhibit host-mediated anti-tumor activity; but the structure of this compound differs markedly from that of the compounds provided by the present invention. Lastly, Kobayashi S. et al., in "Synthesis and Immulogical Activities of Muramyl Dipeptide Derivatives", presented at the 7th Symposium on Progress in Organic Reactions and Synthesis, in Gifu, Japan, in 1980 reports dipeptides having immunological activity and expected to have anti-tumor activity; but again these differ in structure from the compounds of the present invention.

Thus, to the best of our knowledge, the literature does not disclose any immunoregulatory or anti-neoplastic agents with a structure of the type possessed by the compounds which we now provide.

BRIEF SUMMARY OF INVENTION

The compounds which are provided by the present invention are those of the formula:

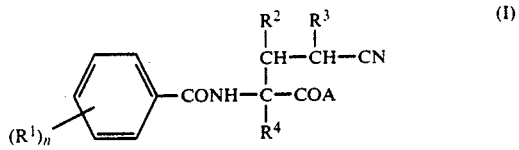

wherein:
n is an integer from 1 to 5;
R¹ is a hydrogen atom, an alkyl group, a haloalkyl group, a halogen atom, a mercapto group, an alkylmercapto group, a hydroxy group, an alkoxy group, an acyloxy group, a carboxyl group, an alkoxycarbonyl group, an amino group, an alkyl-substituted amino group, an aryl-substituted amino group, an acylamino group, a haloalkoxycarbonylamino group, an alkanesulphonyl group, a nitro group or a cyano group (and, when n is an integer from 2 to 5, the radicals R¹ may be the same or different);

R² and R³ may be the same or different and each is a hydrogen atom or an alkyl group;

R⁴ is a hydrogen atom, an alkyl group, a cyano group, a cyanoalkyl group, a hydroxyalkyl group, an alkoxycarbonyl group, a carboxyl group, an aryl group, an aralkyl group, a mercaptoalkyl group, an alkylthioalkyl group, or a thioalkyl group (the free bond of the sulphur in said thioalkyl group being joined to the sulphur of another moiety of the same formula); and A is a hydroxy group, an alkoxy group, an amino group, an alkyl-substituted amino group (optionally halogen- or carbamoyl-substituted in the alkyl moiety), a hydrazino group, an alkyl- or aryl-substituted hydrazino group, a hydroxylamino group, an alkoxyamino group or an aralkyloxyamino group;
and the pharmaceutically acceptable salts thereof.

The invention further provides several methods for preparing the said compounds of formula (I) and their pharmaceutically acceptable salts.

The invention still further provides a pharmaceutical composition, useful for immunoregulatory or anti-tumor treatment, which comprises a compound of the said formula (I) or a pharmaceutically acceptable salt thereof, together with a pharmaceutically acceptable carrier or diluent.

DETAILED DESCRIPTION OF INVENTION

In the compounds of formula (I), where R¹ represents an alkyl group, it may be straight or branched and preferably has from 1 to 4 carbon atoms, for example methyl, ethyl, propyl, isopropyl or t-butyl.

Where R¹ represents a haloalkyl group, it preferably has 1 or 2 carbon atoms, for example trifluoromethyl or 2,2,2-trichloroethyl.

Where R¹ represents a halogen atom, it may be chlorine, bromine, iodine or fluorine.

Where R¹ represents an alkylmercapto group, it may be straight or branched and preferably has from 1 to 16 carbon atoms, for example methylthio, ethylthio, propylthio, isopropylthio, butylthio, t-butylthio or hexadecylthio.

Where R¹ represents an alkoxy group, it may be straight or branched and preferably has from 1 to 16 carbon atoms, for example methoxy, ethoxy, propoxy, isopropoxy, butoxy, t-butoxy or hexadecyloxy.

Where R¹ represents an acyloxy group, it is preferably a straight or branched alkanoyloxy group having from 2 to 16 carbon atoms or a benzoyloxy group which may optionally be substituted in the aromatic ring. Examples of the alkanoyloxy group are acetoxy, propanoyloxy, butyryloxy, isobutyryloxy, pivaloyloxy and palmitoyloxy. The benzoyloxy group may optionally be substituted in the aromatic ring with one or more alkyl groups (e.g. methyl, ethyl, propyl or isopropyl), lower alkoxy groups (e.g. methoxy, ethoxy, propoxy or isopropoxy), halogen atoms (e.g. chlorine, bromine, iodine or fluorine), nitro groups, trifluoromethyl groups, cyano groups, hydroxy groups, amino groups or carboxyl groups.

Where R¹ represents an alkoxycarbonyl group, it may be straight or branched and preferably has from 2 to 17 carbon atoms, for example methoxycarbonyl, ethoxycarbonyl, propoxycarbonyl, isopropoxycarbonyl, butoxycarbonyl, isobutoxycarbonyl, t-butoxycarbonyl or hexadecyloxycarbonyl.

Where $R^1$ is an alkyl-substituted amino group, the alkyl substituent or substituents may be straight or branched and are preferably lower alkyl groups. Examples of such alkyl-substituted amino groups are methylamino, ethylamino, propylamino, isobutylamino, dimethylamino, diethylamino and diisopropylamino.

Where $R^1$ is an aryl-substituted amino group, it may be for example a phenylamino group. The aryl substituent may, optionally, in turn be substituted in the aromatic ring with, for example, one or more lower alkyl groups such as methyl, ethyl, propyl or isopropyl, lower alkoxy groups such as methoxy, ethoxy, propoxy or isopropoxy, halogen atoms such as chlorine, bromine, iodine or fluorine, nitro groups, trifluoromethyl groups, hydroxy groups, amino groups or carboxyl groups.

Where $R^1$ is a acylamino group, it can be a straight or branched alkanoylamino group preferably having from 2 to 16 carbon atoms, for example acetylamino, propionylamino, butyrylamino, isobutyrylamino, pivaloylamino or palmitoylamino. Alternatively, it may be a benzoylamino group, which may optionally be substituted in the aromatic ring, preferably with one or more lower alkyl groups (e.g. methyl, ethyl, propyl or isopropyl), lower alkoxy groups (e.g. methoxy, ethoxy, propoxy or isopropoxy), halogen atoms (e.g. chlorine, bromine, iodine or fluorine), nitro groups, trifluoromethyl groups, hydroxy groups, amino groups or carboxyl groups.

Where $R^1$ represents a haloalkoxycarbonylamino group, it is preferably 2,2,2-trichloroethoxycarbonylamino or 2,2,2-tribromoethoxycarbonylamino.

Where $R^1$ represents an alkanesulphonyl group, it preferably has from 1 to 4 carbon atoms, for example methanesulphonyl, ethanesulphonyl, propanesulphonyl or butanesulphonyl.

Where either $R^2$ or $R^3$ represents an alkyl group, it may be straight or branched and it preferably has from 1 to 3 carbon atoms, for example methyl, ethyl, propyl or isopropyl.

Where $R^4$ represents an alkyl group, it may be straight or branched and preferably has from 1 to 4 carbon atoms, for example methyl, ethyl, propyl, isopropyl, butyl, isobutyl or t-butyl.

Where $R^4$ is a cyanoalkyl group, it preferably has from 1 to 4 carbon atoms in the alkyl moiety, for example cyanomethyl, 2-cyanoethyl, 3-cyanopropyl or 4-cyanobutyl.

Where $R^4$ represents a hydroxyalkyl group, it preferably has from 1 to 4 carbon atoms in the alkyl moiety, for example hydroxymethyl, 2-hydroxyethyl or 4-hydroxybutyl.

Where $R^4$ is an alkoxycarbonyl group, it may be straight or branched and preferably has from 1 to 4 carbon atoms in the alkoxy moiety, for example methoxycarbonyl, ethoxycarbonyl, propoxycarbonyl, butoxycarbonyl or isobutoxycarbonyl.

Where $R^4$ represents an aryl group, it is preferably phenyl and may optionally be substituted in the aromatic ring, for example with one or more lower alkyl groups (such as methyl, ethyl, propyl or isopropyl), lower alkoxy groups (such as methoxy, ethoxy, propoxy or isopropoxy), trifluoromethyl groups, cyano groups, hydroxy groups, nitro groups, amino groups or halogen atoms (such as fluorine, chlorine or bromine).

Where $R^4$ represents an aralkyl group, it is preferably benzyl, phenethyl or phenylpropyl and may optionally be substituted in the aromtic ring, for example with any of the substituents mentioned above for the case where $R^4$ represents aryl.

Where $R^4$ represents a mercaptoalkyl group, it preferably has from 1 to 4 carbon atoms in the alkyl moiety, for example mercaptomethyl, mercaptoethyl, mercaptopropyl or mercaptobutyl.

Where $R^4$ represents an alkylthioalkyl group, each of the alkyl moieties preferably has from 1 to 4 carbon atoms, for example methylthiomethyl, methylthioethyl, methylthiobutyl or propylthioethyl.

Where $R^4$ represents a thioalkyl group, the alkyl moiety preferably has from 1 to 4 carbon atoms. The free bond of the sulphur atom in the thioalkyl group is joined to the sulphur atom of a group of the same formula, so that the compound of formula (I) will then have a symmetrical structure of the overall formula:

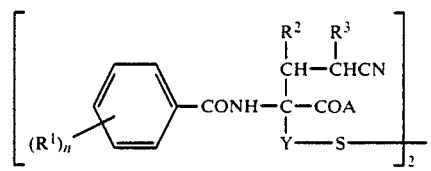

wherein n, $R^1$, $R^2$, $R^3$ and A have the meanings already given, and Y is a bivalent saturated aliphatic hydrocarbon radical (preferably having from 1 to 4 carbon atoms).

Where A is an alkoxy group, it may be straight or branched and preferably has from 1 to 16 carbon atoms, for example methoxy, ethoxy, propoxy, isopropoxy, butoxy, isobutoxy, hexyloxy, decyloxy or hexadecyloxy.

Where A is an alkyl-substituted amino group, the alkyl moiety preferably has from 1 to 4 carbon atoms, for example methylamino, dimethylamino, ethylamino, diethylamino, propylamino, isopropylamino, butylamino or isobutylamino. The alkyl moiety may optionally itself be halogen- or carbamoyl-substituted, for example 2-chloroethylamino, 2-bromoethylamino, 3-chloropropylamino, 2-carbamoylethylamino or 3-carbamoylpropylamino.

Where A represents an alkyl-substituted hydrazino group, it preferably has from 1 to 4 carbon atoms in the or each alkyl moiety, for example methylhydrazino, N,N-dimethylhydrazino, ethylhydrazino or N,N-diethylhydrazino.

Where A represents an aryl-substituted hydrazino group, it is preferably phenylhydrazino. It may also be substituted in the aromatic ring, for example with one or more lower alkyl groups (such as methyl, ethyl, propyl or isopropyl), lower alkoxy groups (such as methoxy, ethoxy, propoxy or isopropoxy), or halogen atoms (such as fluorine, chlorine or bromine).

Where A represents an alkoxyamino group, it preferably has from 1 to 4 carbon atoms in the alkoxy moiety, for example methoxyamino, ethoxyamino, propoxyamino or isopropoxyamino.

Where A represents an aralkyloxyamino group, it is preferably benzyloxyamino. It may also optionally be substituted in the aromatic ring, for example with one or more of the lower alkyl groups, lower alkoxy groups or halogen atoms mentioned as the optional substituents for where $R^4$ represents aryl-substituted hydrazino.

Preferred compounds among those of formula (I), by reason of their pharmaceutical activity and ease of synthesis, are those wherein:

$R^1$ is a hydrogen atom, a halogen atom, an alkyl group, a hydroxy group, a cyano group or an alkoxycarbonyl group;

$R^2$ and $R^3$ are both hydrogen atoms;

$R^4$ is an alkyl group, a carboxyl group or an alkoxycarbonyl group;

A is a hydroxy group or an alkoxy group; and n is 1 or 2;

and the pharmaceutically acceptable salts thereof.

In particular, the following compounds are most highly preferred, that is to say those wherein:

$R^1$ is a halogen atom, particularly chlorine;

$R^2$ and $R^3$ are both hydrogen;

$R^4$ is an alkyl group having from 1 to 4 carbon atoms, particularly methyl;

A is a hydroxy group or an alkoxy group having from 1 to 4 carbon atoms; and n is 1;

and the pharmaceutically acceptable salts thereof, particularly the sodium salts.

The compounds of formula (I) can be prepared by a variety of methods, which are as follows.

Method 1

Those compounds having the formula:

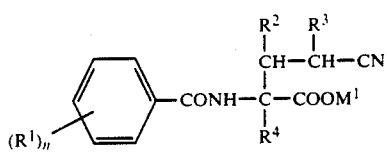

(wherein $R^1$, $R^2$, $R^3$, $R^4$ and n are as defined above, and $M^1$ is an alkyl group)

can be obtained by reacting an amino-acid derivative of formula:

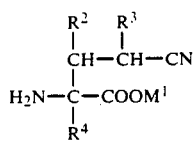

(wherein $R^2$, $R^3$, $R^4$ and $M^1$ are as defined above) with an acid halide of formula:

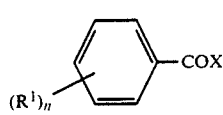

(wherein $R^1$ and n are as defined above, and X is a halogen atom, e.g. chlorine or bromine)

in the presence of a base and an inert solvent.

The reaction proceeds stoichiometrically, using the reactants in equimolar amounts. It is carried out in the presence of a base, which may be an organic base such as tertiary amine (e.g., triethylamine, dimethylaniline, diethylaniline or pyridine), or an inorganic base such as alkaline metal hydroxide (e.g. potassium hydroxide), an alkali metal bicarbonate (e.g. potassium bicarbonate or sodium bicarbonate) or an alkaline earth metal hydroxide (e.g. calcium hydroxide or magnesium hydroxide).

If an organic solvent is employed for the reaction, then it is preferably carried out in the presence of a tertiary amine. On the other hand, if the reaction solvent is a mixture of an organic solvent and water, then it is preferably carried out in the presence of an alkali metal bicarbonate, such as sodium bicarbonate or potassium bicarbonate.

There is no particular limitation on the choice of reaction solvent, for example, the solvent may be an alcohol, such as methanol, ethanol, propanol, isopropyl alcohol or butanol; an aromatic hydrocarbon, such as benzene, toluene or xylene; a ketone, such as acetone, methyl butyl ketone or methyl amyl ketone; a halogenated hydrocarbon, such as tetrachloroethane, chlorobenzene or dichlorobenzene; a nitrile, such as benzonitrile or acetonitrile; an amide, such as N,N-dimethylformamide, N,N-dimethylacetamide or hexamethylphosphoric triamide; dimethylsulphoxide; a mixture of any of these solvents; or a mixture of any of these solvents with water.

The reaction temperature also is not particularly critical, but a temperature from −20° C. to 100° C. is usually employed, preferably from 0° C. to 30° C. The reaction time will vary, depending upon the nature of the starting materials and on the reaction temperature, but will usually be from 1 to 5 hours.

On completion of the reaction, the desired product of formula (IV) can be recovered from the reaction mixture by conventional means. For example, if the desired product is precipitated in the reaction mixture, it may be recovered by filtration. If it is not precipitated, the product may be recovered by distilling off the solvent from the reaction mixture. If necessary, the product thus obtained may be further purified, for instance by recrystallisation, vacuum distillation or chromatography.

The amino-acid derivatives of formula (II), employed as starting materials in this reaction, can be prepared by the method disclosed in Tetrahedron Letters, No. 17, pp 1455–1458 (1977). Thus, a Schiff base of formula:

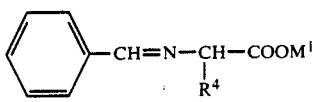

(wherein $R^4$ and $M^1$ are as defined above) is reacted with a compound having the formula:

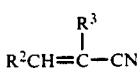

(wherein $R^2$ and $R^3$ are as defined above) in the presence of a strong base, for example trimethylbenzylammonium hydroxide (available as a 40% methanol solution under the Trade mark "Triton B"), 1,5-diazabicyclo[4.3.0]-5-nonene (DBN) or 1,8-diazabicyclo[5.4.0]-7-undecene (DBU), giving a compound of formula:

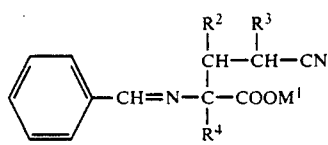

(wherein $R^2$, $R^3$, $R^4$ and $M^1$ are as defined above) hydrolyzing this compound with an acid (e.g. a mineral acid such as hydrochloric acid) and neutralizing the resulting product with a base. The hydrolysis gives a salt of the desired amino-acid derivative of formula (II), having the formula:

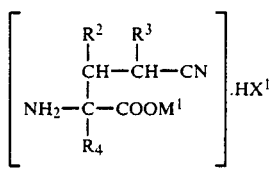

(wherein $R^2$, $R^3$, $R^4$ and $M^1$ are as defined above, and $X^1$ is a halogen atom or a sulphate group) and this can be employed directly in the reaction with the acid halide of formula (III), in an aqueous reaction mixture, without isolating the free compound.

The compound of formula (IV) thus obtained can be hydrolysed with an alkali metal hydroxide in water or an aqueous organic solvent, to give a metal salt of the corresponding carboxylic acid derivative, having the formula:

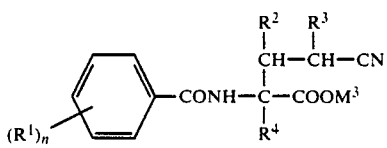

(wherein $M^3$ is an alkali metal, such as sodium or potassium, and $R^1$, $R^2$, $R^3$, $R^4$ and n are as defined above).

This reaction proceeds stoichiometrically, using the reactants in equimolar amounts; but it is preferred to employ an excess of the alkali metal hydroxide, by using from 1.0 to 2.0 moles of the alkali metal hydroxide per mole of the compound (IV).

If an aqueous organic solvent is used for this reaction step, there is no particular limitation on the choice of the organic solvent, provided that it does not interfere with the reaction. For example, it may be an alcohol, such as methanol, ethanol, propanol, isopropyl alcohol or butanol; or a ketone, such as acetone or methyl butyl ketone. The alkali metal hydroxide may be, for example, sodium hydroxide or potassium hydroxide. The reaction temperature is preferably from 0° C. to 50° C.

On completion of this reaction, the desired product of formula (V) can be recovered from the reaction mixture by conventional means. For example, if it is precipitated out, it can be recovered by filtration and washed with a non-solvent for the product. If it is not precipitated out, then an alcohol (e.g. methanol or ethanol) or a ketone (e.g. acetone or methyl ethyl ketone) can be added to the reaction mixture, in order to precipitate it, and the precipitate is then collected as usual.

The product of formula (V) thus obtained can be neutralized with an acid in water or in an aqueous organic solvent, in the conventional manner, to give the free carboxylic acid having the formula:

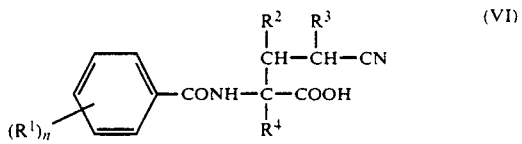

(wherein $R^1$, $R^2$, $R^3$, $R^4$ and n are as defined above). The desired product (VI) can be recovered from the reaction mixture by conventional means. For example, if it is precipitated out in the reaction mixture, it can be recovered by filtration. If the product is not precipitated, it can be recovered by distilling off the solvent, extracting the residue with a water-immiscible organic solvent, and distilling off the solvent from the extract. There is no particular limitation on the choice of the water-immiscible solvent used for this extraction: for example it may be an ether such as dimethyl ether or diethyl ether; a halogenated hydrocarbon, such as dichloromethane or chloroform; an aromatic hydrocarbon, such as benzene, toluene or xylene; or an ester, such as ethyl acetate. If necessary, the resulting product (IV) can be further purified, for example by recrystallisation or chromatography.

Method 2

The compounds having the formula (IV), as defined above, can also be prepared by reacting an amino acid derivative of formula:

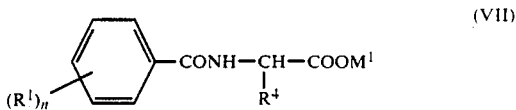

(wherein $R^1$, $R^4$, $M^1$ and n are as defined above) with a compound of formula:

(wherein $R^2$ and $R^3$ are as defined above) in the presence of a strong base.

This reaction proceeds stoichiometrically, using the reactants in equimolar amounts; but it is preferred to employ an excess of the compound (VIII) and of the base, by using from 1.0 to 1.5 moles of each per mole of the compound (VII). The strong base may suitably be, for example, 1,5-diazabicyclo[4.3.0]-5-nonene (DBN), 1,8-diazabicyclo[5.4.0]-7-undecene (DBU), or a metal hydride such as sodium hydride or potassium hydride. There is not particular limitation on the choice of solvent used for this reaction, provided that it does not interfere with the reaction, and suitable solvents include halogenated hydrocarbons such as chloroform, dichloromethane or dichloroethane, ethers such as dimethyl ether, diethyl ether, diisopropyl ether, dioxane or tetrahydrofuran, and amides such as N,N-dimethylformamide, N,N-diethylacetamide or hexamethylphosphoric triamide. The reaction temperature is suitably from 0° C. to 50° C., and preferably from 20° C. to 30° C. The reaction time will vary, depending upon the nature of the starting materials and the reaction temperature, but it is usually from 2 to 20 hours.

On completion of the reaction, the desired product can be obtained by washing the reaction mixture with water and distilling off the solvent. If necessary, the product thus obtained can be further purified, for example, by recrystallisation, vacuum distillation or chromatography.

Method 3

Those compounds having the formula:

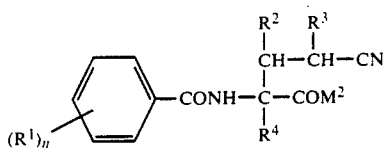

(wherein $R^1$, $R^2$, $R^3$, $R^4$ and n are as defined above; and $M^2$ has the same meaning as A defined above, other than hydroxy or alkoxy) can be obtained by reacting an oxazolone of formula:

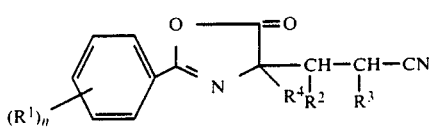

(wherein $R^1$, $R^2$, $R^3$, $R^4$ and n are as defined above) with an organic base of formula:

$$HM^2 \qquad (X)$$

(wherein $M^2$ is as defined above).

The reaction proceeds stoichiometrically, using the reactants in equimolar amounts; but it is preferred to have an excess of the base (X), by using from 1.0 to 1.5 moles of it per mole of the oxazolone (IX). There is no particular limitation on the choice of solvent for this reaction, provided that it does not interfere with the reaction, and suitable examples are hydrocarbons such as benzene, toluene or xylene, ethers such as dioxane, tetrahydrofuran or diisopropylether, and halogenated hydrocarbons such as dichloroethane or chloroform. The reaction tempareture used is suitably from 0° C. to 100° C., more preferably from 20° C. to 50° C. The reaction time will generally be from 2 to 12 hours.

Upon completion of the reaction, the desired product (XI) can be obtained by washing the reaction mixture with water and distilling off the solvent. If necessary, the product can be further purified, for example by recrystallisation or chromatography.

The oxazolone starting materials of formula (IX) can be prepared by the method disclosed in the Journal fur Praktische Chemie [2], 82, 60 (1910).

Method 4

The amino-acids of formula:

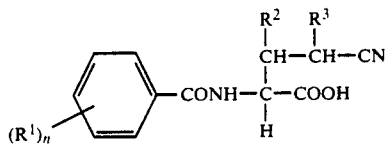

(wherein $R^1$, $R^2$, $R^3$ and n are as defined above) can be prepared by heating a compound having the formula:

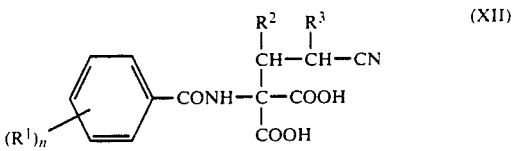

(wherein $R^1$, $R^2$, $R^3$ and n are as defined above).

For this reaction, the compound (XII) can be dissolved in any solvent which will not interfere with the reaction, for example an ether such as diisopropyl ether, tetrahydrofuran or dioxane, or a hydrocarbon such as benzene, toluene or xylene. An organic base such as triethylamine, dimethylaniline or pyridine can be added in order to make the reaction run more smoothly. Alternatively, the starting material (XII) can be dissolved directly in a tertiary organic base, such as pyridine or diethylaniline, and the resulting solution heated to obtain the desired product (XIII). The temperature used for the reaction is suitably from 30° C. to 100° C., more preferably from 50° C. to 100° C.; and the reaction time is generally from 1 to 8 hours.

Upon completion of the reaction, the desired product (XIII) can be recovered by conventional means. For instance, if the reaction has been performed in the presence of an organic base, the product (XIII) can be obtained by washing the reaction mixture with water and distilling off the organic solvent. If necessary, the product can be further purified, for example by recrystallisation, vacuum distillation or chromatography.

The acid of formula (XIII) can also be esterified to give a compound of the above formula (IV), wherein $R^4$ represents hydrogen, by reacting it with a suitable alkylating agent. This esterification can be carried out by conventional techniques; but it is preferred to perform it in an amide solvent, such as N,N-dimethylformamide, N,N-diethylacetamide or hexamethylphosphoric triamide. The alkylating agents may suitably be an alkyl halide, in which case the reaction is preferably carried out in the presence of a base, for instance an alkali metal carbonate such as potassium carbonate or sodium carbonate.

The compounds of formula (I) which are carboxylic or hydroxamic acids can be salified in the conventional manner, so as to obtain their pharmaceutically acceptable salts—for example, salts with inorganic metals such as lithium, sodium, potassium, calcium, magnesium or aluminium, and ammonium or substituted ammonium salts, such as the cyclohexylammonium, diisopropylammonium or triethylammonium salts. In general, the sodium, potassium and calcium salts are preferred.

The compounds of the invention exhibit optical isomerism. It should be understood that the individual optical isomers are included within the scope of the invention, as well as the racemic mixtures of isomers. However, it will also be understood that, for each pair of optical isomers of the compounds of the invention, one of the individual isomers may exhibit substantially greater pharmaceutical activity than the other isomer or the racemic mixture, as is commonly known also for other pharmaceutical compounds which exhibit optical isomerism.

In general, racemic mixtures of the compounds of the invention, prepared by the methods described above, can be used without resolution into the individual isomers. However, if desired, the individual optical isomers can be obtained, using per se conventional techniques, either by resolving the racemic mixtures or by stereo-specific synthesis using starting materials or intermediates of known configuration. For example, when using Method 1 described above, the N-benzyloxycarbonyl-L-prolyl derivative of the starting material (II) is prepared, the two diastereoisomers of the derivative are separated, and the prolyl protecting groups are removed, leaving the two isomers of the compound (II) which can then be reacted with the acid halide (III) in a stereo-specific synthesis of the optical isomers of the final product (IV).

We have discovered that the compounds of the invention are useful medically, by virtue of possessing valuable immunoregulatory and anti-tumor activities. These activities are illustrated by the following experiments.

(1) Recovery of immune function in tumor-bearing mice

ICR/JcI female mice implanted with Ehrlich carcinoma cells were used to examine the effect of compounds of this invention on delayed-type hypersensitivity reactions induced by injecting BCG (Bacillus Calmette-Guerin) into the footpad.

Each test group consisted of 10 mice. Each mouse was immunized subcutaneously with 500 micrograms of BCG. On the ninth day before immunization, $2 \times 10^6$ Ehrlich carcinoma cells were transplanted subcutaneously into each mouse. On the fourth and second days before immunization, the test compound was administered intraperitoneally, at a dose of either 1 or 10 mg/kg of body weight. On the 14th day after immunization, a challenge injection was given intradermally into the footpad of one of the hind legs; and the swelling of the footpad was examined 24 hours after this challenge injection, by comparing it with the footpad not injected with BCG. Control groups of normal and tumor-bearing animals were similarly injected with BCG and the swelling of the footpad measured.

The recovery of immune response in the tumor-bearing animals treated with the test compounds was calculated by means of the following formula:

Recovery of immune response
(%) = 100 − [(A/B) × 100]

wherein:
A = (Swelling of footpad of control group of normal animals—Swelling of footpad of tumor-bearing animals given test compound)
B = (Swelling of footpad of control group of normal animals—Swelling of footpad of control group of tumor-bearing animals).

The results obtained are shown in Table 1 and demonstrate the effectiveness of the compounds of the invention, in the recovery of immune response in the tumor-bearing mice.

TABLE 1

| Test Compound | Recovery of immune response (%) | |
|---|---|---|
| | 1 mg/kg | 10 mg/kg |
| N—(p-chlorobenzoyl)-2-(2-cyanoethyl)alanine | 67 | 99 |
| N—(p-chlorobenzoyl)-2-(2-cyanoethyl)alanine methyl ester | 45 | 121 |

TABLE 1-continued

| Test Compound | Recovery of immune response (%) | |
|---|---|---|
| | 1 mg/kg | 10 mg/kg |
| N—(p-chlorobenzoyl)-2-(2-cyanoethyl)phenylglycine methyl ester | 71 | 114 |
| N—(4-chloro-2-hydroxybenzoyl)-2-(2-cyanoethyl)alanine methyl ester | 60.9 | 58.6 |
| Disodium 2-(p-chlorobenzoylamino)-2-(2-cyanoethyl)malonate dihydrate | 42.7 | 92.8 |

The above test was repeated with the test compound N-(p-chlorobenzoyl)-2-(2-cyanoethyl)alanine methyl ester, but administered orally instead of intraperitoneally. The recovery of immune response was 81% at a dose of 1 mg/kg and 116% at a dose of 10 mg/kg. These results demonstrate the effectiveness of the compound when administered by the oral, as well as the intraperitoneal, route.

(2) Antitumor effect on Sarcoma-37 solid tumor in mice

Sarcoma-37 cells ($2 \times 10^6$ were implanted subcutaneously into the axillary region of 7-week old female ICR/Jcl mice. The test compounds shown in Table 2 were administered intraperitoneally, at the doses shown (in mg/kg body weight/day), once a day on each of the first to 14th and 7th to 10th days after implantation. As well as the compounds of the invention, two control compounds were used which have been reported to possess immunoregulatory and anti-tumor activities: levamisole (the laevo-isomer of tetramisole) and tilorone. These control compounds were administered at the doses shown because higher doses exhibited acute toxicity in the test animals. An unmedicated control group of animals was also used.

On the 21st day after implantation, the diameter of the tumor was measured and compared with that in the control group, so as to evaluate the percentage suppression of tumor growth.

The results are shown in Table 2.

TABLE 2

| Tested Compound | Dose | Suppression of tumor growth (%) on day 21 |
|---|---|---|
| N—(p-chlorobenzoyl)-2-(2-cyanoethyl)alanine methyl ester | 1 | 8 |
| | 3 | 26 |
| | 10 | 35 |
| | 30 | 39 |
| | 100 | 33 |
| N—(o-acetoxybenzoyl-2-(2-cyanoethyl)alanine methyl ester | 1 | 32 |
| N—(o-hydroxybenzoyl)-2-(2-cyanoethyl)alanine methyl ester | 1 | 38 |
| N—(3,4-dihydroxybenzoyl)-2-(2-cyanoethyl)alanine methyl ester | 10 | 55 |
| N—(3-fluoro-4-methylbenzoyl)-2-(2-cyanoethyl)alanine methyl ester | 1 | 27 |
| | 10 | 41 |
| Disodium 2-(p-chlorobenzoylamino)-2-(2-cyanoethyl)-malonate dihydrate | 10 | 27 |
| Disodium 2-(p-methylbenzoylamino)-2-(2-cyanoethyl)-malonate monohydrate | 10 | 26 |
| N—(2-amino-4-chlorobenzoyl)-2-(2-cyanoethyl)alanine | 10 | 26 |

TABLE 2-continued

| Tested Compound | Dose | Suppression of tumor growth (%) on day 21 |
|---|---|---|
| methyl ester N—(p-chlorobenzoyl)-2- (2-cyanoethyl)methionine methyl ester | 10 | 47 |
| (Control compounds) | | |
| Levamisole | 3 | 0 |
| Tilorone | 30 | −5 |

(3) Anti-tumor activity against syngeneic tumor MM-46

Mouse mammary tumor cells ($2 \times 10^6$) were inoculated subcutaneously into the axillary region of 7-week old C3H/He mice, and the test compounds shown in Table 3 were administered intraperitoneally once a day, at the doses indicated (in mg/kg body weight/day), on each of the third to 10th days after implantation. On the 30th day after implantation, the tumor diameter was measured and compared with that taken from a control group of unmedicated animals. On the 45th day after implantation, the number of animals in each group with complete regression of the tumor was noted, and the percentage for the group calculated.

The results are shown in Table 3.

TABLE 3

| Tested Compound | Dose | Suppression of tumor growth (%) on day 30 | Complete regression of tumor on day 45 (and % for group) |
|---|---|---|---|
| N—(p-chlorobenzoyl)- 2-(2-cyanoethyl)- alanine methyl ester | 3 | −3 | 0/5 (0%) |
| | 10 | 30 | 2/5 (40%) |
| | 30 | 36 | 2/5 (40%) |
| | 100 | 39 | 2/5 (40%) |
| (Control compounds) | | | |
| Levamisole | 3 | 14 | 1/5 (20%) |
| Tilorone | 30 | 9 | 1/5 (20%) |

(4) Acute toxicity test

The compound of the invention, N-(p-chlorobenzoyl)-2-(2-cyanoethyl)alanine methyl ester, was administered intraperitoneally to ddy mice at doses of 100 and 300 mg/kg of body weight. One week after administration, none of the mice had died and there was no retardation in their rate of body weight gain.

The results of the pharmacological tests indicate that the compounds of the invention are valuable as immune-regulators for use against cancers, bacterial infections and auto-immune diseases, and as host-mediated anti-tumor agents. They are suitable for administration medically by the normal parenteral, enteral and oral routes, using the conventional types of formulation, for example by subcutaneous, intravenous or intramuscular injection, as suppositories, or orally in the form of tablets, capsules, powders, granules and syrups.

The pharmaceutical compositions provided in accordance with the invention therefore comprise at least one compound of the above formula (I), or a pharmaceutically acceptable salt thereof, together with a pharmaceutically acceptable carrier or diluent. The carrier or diluent used may be liquid or solid and its choice will depend upon the intended type of formulation and method of administration. The composition may also contain conventional pharmaceutical adjuvants suited to the type of formulation in question.

The preparation of the compounds and compositions in accordance with the invention is illustrated by the following non-limiting Examples. The Preparation which follows the Examples illustrates the synthesis of one of the starting materials of formula (IX) above.

EXAMPLE 1

N-(p-Chlorobenzoyl)-2-(2-cyanoethyl)alanine methyl ester and N-(p-chlorobenzoyl)-2-(2-cyanoethyl)alanine 2-(2-Cyanoethyl)alanine methyl ester (7.8 g) was dissolved in 100 ml of dichloromethane and 8.7 g of p-chlorobenzoyl chloride were added dropwise to the resulting solution at 5° C., followed by the addition of 6.0 g of triethylamine at the same temperature. The reaction mixture was then stirred at 0°–5° C. for one hour, and then washed with two 100 ml portions of water. The organic layer was separated off and dried over magnesium sulphate, and the solvent was distilled off. The resulting residue was purified by column chromatography on silica gel (eluent: a 9:1 mixture of benzene and ethyl acetate) and recrystallized from ethyl acetate, to give 12.4 g of the desired methyl ester as colourless needles melting at 91°–92° C.

Elementary analysis: Calculated for $C_{14}H_{15}O_3N_2Cl$: C, 57.05; H, 5.13; N, 9.50; Cl, 12.03%; Found: C, 56.81; H, 5.11; N, 9.20; Cl, 12.06%

29.4 g of N-(p-chlorobenzoyl)-2-(2-cyanoethyl)alanine methyl ester were dissolved in 100 ml of methanol, 150 ml of a 1N solution of sodium hydroxide were added thereto at 5° C., and the mixture was stirred at 0°–5° C. for 3 hours. The reaction mixture was then diluted with 100 ml of water and washed with ethyl acetate (300 ml). The aqueous layer was separated off, adjusted to pH 2.0 by adding concentrated hydrochloric acid at 5° C., and extracted with ethyl acetate (300 ml). The extract was dried over magnesium sulphate and the solvent was distilled off. The resulting residue was recrystallized from diethyl ether, to afford 21.6 g of the desired amino-acid as a colourless powder melting at 82°–85° C.

Elementary analysis: Calculated for $C_{13}H_{13}O_3N_2Cl$: C, 55.62; H, 4.67; N, 9.98; Cl, 12.63%; Found: C, 55.57; H, 4.85; N, 9.57; Cl, 12.34%

The following compounds were obtained by using the method of the preceding Example:

| | |
|---|---|
| N—(p-Chlorobenzoyl)-2-(2-cyanoethyl)phenylglycine methyl ester | Melting point: 127–128° C. |
| 2-(2-Cyanoethyl)-N—benzoylalanine methyl ester | Melting point: 127–128° C. |
| 2-(p-Chlorobenzamido)-4-cyano-2-(2-cyanoethyl)butyric acid methyl ester | Melting point: 168–169° C. |
| 2-(2-Cyanoethyl)-N—benzoylaminomalonic acid diethyl ester | Melting point: 61–62° C. |
| 2-(2-Cyanoethyl)-N—benzoylphenylglycine ethyl ester | Melting point: 71–72° C. |
| 2-(2-Cyanoethyl)-N—(p-chlorobenzoyl)alanine hexadecyl ester | Melting point: 83–84° C. |
| N—(p-Chlorobenzoyl)-2-(2-cyanoethyl)aminomalonic acid diethyl ester | Melting point: 82–83° C. |
| N—(p-Chlorobenzoyl)-2-(2-cyanoethyl)serine methyl ester | Melting point: 117–118° C. |
| N—(p-Chlorobenzoyl)-2-(2-cyanoethyl)leucine methyl ester | Melting point: 48–51° C. |
| N—(m-Chlorobenzoyl)-2-(2-cyanoethyl)alanine methyl ester | $n_D^{25} = 1.5365$ |
| N—(m-Chlorobenzoyl)-2-(2-cyanoethyl)alanine | Melting point: 86–89° C. |
| N—(o-Chlorobenzoyl)-2-(2-cyanoethyl)alanine methyl ester | Melting point: 73–74° C. |
| N—(o-Chlorobenzoyl)-2-(2-cyanoethyl)alanine | Melting point: 100–102° C. (with decomposition) |
| 2-(2-Cyanoethyl)-N—(2,4-dichloro- | $n_D^{25} = 1.5415$ |

-continued

| | |
|---|---|
| benzoyl)alanine methyl ester | |
| 2-(2-Cyanoethyl)-N—(2,4-dichloro-benzoyl)alanine | Melting point: 151-153° C. |
| 2-(2-Cyanoethyl)-N—(p-fluorobenzoyl)alanine methyl ester | Melting point: 111-112° C. |
| 2-(2-Cyanoethyl)-N—(p-fluorobenzoyl)alanine | Melting point: 85-88° C. |
| 2-(2-Cyanoethyl)-N—(p-bromobenzoyl)alanine methyl ester | Melting point: 108-109° C. |
| 2-(2-Cyanoethyl)-N—(p-bromobenzoyl)alanine | Melting point: 87-89° C. |
| N—(p-Chlorobenzoyl)-2-(2-cyanoethyl)glycine methyl ester | Melting point: 110-111° C. |
| N—(p-Chlorobenzoyl)-2-(2-cyanoethyl)glycine | Melting point: 152-154° C. |
| 2-(2-Cyanoethyl)-N—(p-toluoyl)-alanine methyl ester | Melting point: 111-112° C. |
| 2-(2-Cyanoethyl)-N—(p-toluoyl)-alanine | Melting point: 84-86° C. |
| 2-(2-Cyanoethyl)-N—(p-iodobenzoyl)-alanine methyl ester | Melting point: 114-115° C. |
| 2-(2-Cyanoethyl)-N—(p-iodobenzoyl)-alanine | Melting point: 87-89° C. |
| 2-(2-Cyanoethyl)-N—(pentafluorobenzoyl)alanine methyl ester | $n_D^{25} = 1.4710$ |

EXAMPLE 2

N-(p-Chlorobenzoyl)-2-(2-cyanoethyl)phenylglycine methyl ester

To 100 ml of a solution of 6.0 g of N-(p-chlorobenzoyl)phenylglycine methyl ester in dichloromethane were added 1.6 g of acrylonitrile and 3.6 g of 1,8-diazabicyclo[5.4.0]-7-undecene followed by stirring at room temperature for 16 hours. The solvent was distilled off and 100 ml of ethyl ether were added to the resulting residue. The mixture was washed with two 100 ml portions of water, and the organic layer was separated off and dried over magnesium sulphate. The solvent was distilled off and the residue was recrystallized from diethyl ether, to give 5.8 g of the desired product as a colourless powder melting at 127°-128° C.

Elementary analysis: Calculated for $C_{19}H_{17}O_3N_2Cl$: C, 63.95; H, 4.80; N, 7.85: Cl, 9.94%; Found: C, 64.04; H, 4.85; N, 7.90; Cl, 9.76%

The following compounds were obtained by using the method of the preceding Example:

| | |
|---|---|
| 2-(2-Cyanoethyl)-N—benzoylphenylglycine ethyl ester | Melting point: 71-72° C. |
| N—(p-Chlorobenzoyl)-2-(2-cyanoethyl)-aminomalonic acid diethyl ester | Melting point: 82-83° C. |
| N—Benzoyl-2-(2-cyanopropyl)phenylglycine ethyl ester | Melting point: 84-85° C. |

EXAMPLE 3

4-Cyano-2-(N-p-chlorobenzamido)-2-methylbutyrylamide 5 ml of a solution of 2.0 g of 2-(p-chlorophenyl)-4-(2-cyanoethyl)-4-methyl-5-oxazolone in tetrahydrofuran were added to a mixture of 9.5 ml of a 28% aqueous ammonia solution and 5 ml of tetrahydrofuran at 5° C., followed by stirring at 0°-5° C. for one hour. The reaction mixture was then extracted with ethyl acetate (50 ml), and the organic layer was separated off and dried over magnesium sulphate. The solvent was distilled off and the resulting residue was recrystallized from diethyl ether, to give 1.8 g of the desired product as a colourless powder melting at 118°-120° C.

Elementary analysis: Calculated for $C_{13}H_{14}O_2N_3Cl$: C, 55.82; H, 5.04; N, 15.02; Cl, 12.67%; Found: C, 55.76; H, 5.27; N, 14.37; Cl, 12.41%

The following compounds were obtained by using the method of the preceding Example:

| | |
|---|---|
| 2-(N—p-Chlorobenzamido)-4-cyano-2-methyl-(N—2-carbamoylethyl)-butyrylamide | Melting point: 138-140° C. |
| 2-(N—p-Chlorobenzamido)-4-cyano-2-methyl-(N—2-chloroethyl)-butyrylamide | Melting point: 172-174° C. |
| 2-(N—p-Chlorobenzamido)-4-cyano-2-methylbutyrylhydroxamide | Melting point: 80-81° C. |
| 2-(N—p-Chlorobenzamido)-4-cyano-2-methyl-(N—dimethyl)butyrylamide | Melting point: 133-134° C. |

EXAMPLE 4

N-(p-Chlorobenzoyl)-2-(2-cyanoethyl)glycine and N-(p-chlorobenzoyl-2-(2-cyanoethyl)glycine methyl ester 20 ml of a solution of 3.2 g of N-(p-chlorobenzoyl)-2-(2-cyanoethyl)aminomalonic acid in pyridine were refluxed for an hour and the solvent was then distilled off. To the resulting residue were added 50 ml of water and 50 ml of ethyl acetate, the mixture was adjusted to pH 2 by adding 3N hydrochloric acid, and the organic layer was separated off and dried over magnesium sulphate. The solvent was distilled off and the resulting residue was recrystallized from ethyl acetate, to afford 2.5 g of the desired amino-acid as colourless granules melting at 152°-154° C.

Elementary analysis: Calculated for $C_{12}H_{11}O_3N_2Cl$: C, 54.05; H, 4.16; N, 10.50; Cl, 13.29%; Found: C, 53.91; H, 4.25; N, 10.29; Cl, 13.09%

1.6 g of methyl iodide and 1.1 g of potassium carbonate were added to 5 ml of a solution of 1.5 g of the acid thus obtained in dimethylformamide. After stirring at room temperature for 16 hours, the reaction mixture was diluted with 50 ml of ethyl acetate and washed with three 50 ml portions of water. The organic layer was separated off and dried over magnesium sulphate. The solvent was distilled off and the resulting residue was recrystallized from diethyl ether, to give 1.3 g of the desired methyl ester as a colourless powder melting at 110°-111° C.

Elementary analysis: Calculated for $C_{13}H_{13}O_3N_2Cl$: C, 55.62; H, 4.67; N, 9.98; Cl, 12.63%; Found: C, 55.78; H, 4.69; N, 10.01; Cl, 12.57%

EXAMPLE 5

N-(3,4-Dihydroxybenzoyl)-2-(2-cyanoethyl)alanine methyl ester 1.56 g of 2-(2-cyanoethyl)alanine methyl ester and 1.4 ml of triethylamine were added to a solution of crude 3,4-diacetoxybenzoyl chloride (prepared from 1.96 g of 3,4-diacetoxybenzoic acid and 2.08 g of phosphorus pentachloride) in 30 ml of dichloromethane, at 5° C. The reaction mixture was stirred at 0°-5° C. for one hour and then washed with 30 ml of water. The organic layer was separated off and dried over magnesium sulphate, and the solvent was distilled off. The resulting residue was dissolved in 10 ml of methanol, 8.3 ml of 28% aqueous ammonia solution were added, and the solution was stirred at room temperature for 23 hours. The mixture was then cooled to 5° C., adjusted to pH 2.0 with concentrated hydrochloric acid, diluted with 50 ml of water, and extracted with two 50 ml portions of dichloromethane. The organic extract was dried over magnesium sulphate, the solvent was distilled off, and the resulting residue was purified by silica gel chromatography (eluent: 2:1 mixture of cyclohexane and ethyl acetate), to give 1.60 g of the desired product as a colourless glass.

Elementary analysis: Calculated for $C_{14}H_{16}N_2O_5$: C, 57.53; H, 5.52; N, 9.58%; Found: C, 57.76; H, 5.58; N, 9.09%

The following compounds were obtained by using the method of the preceding Example:

| | |
|---|---|
| N—(p-Acetoxybenzoyl)-2-(2-cyanoethyl)alanine methyl ester | Melting point: 168–170° C. |
| N—(p-Hydroxybenzoyl)-2-(2-cyanoethyl)alanine methyl ester | Melting point: 106–109° C. |
| N—(p-Methoxybenzoyl)-2-(2-cyanoethyl)alanine methyl ester | Melting point: 112–114° C. |
| N—(p-Nitrobenzoyl)-2-(2-cyanoethyl)alanine methyl ester | Melting point: 96–98° C. |
| N—(p-Cyanobenzoyl)-2-(2-cyanoethyl)alanine methyl ester | Melting point: 115–117° C. |
| N—(o-Acetoxybenzoyl)-2-(2-cyanoethyl)alanine methyl ester | Melting point: 110–112° C. |
| N—(o-Hydroxybenzoyl)-2-(2-cyanoethyl)alanine methyl ester | $n_D^{25} = 1.5377$ |
| N—(p-Methoxycarbonylbenzoyl)-2-(2-cyanoethyl)alanine methyl ester | Melting point: 120–121° C. |
| N—[p-(2,2,2-trichloroethoxycarbonyl)-aminobenzoyl]-2-(2-cyanoethyl)alanine methyl ester | Melting point: 202–204° C. |
| N—(p-Aminobenzoyl)-2-(2-cyanoethyl)alanine methyl ester | Melting point: 125–126° C. |
| N—(3,4-Methylenedioxybenzoyl)-2-(2-cyanoethyl)alanine methyl ester | Melting point: 158–160° C. |
| N—(2-Acetoxy-4-chlorobenzoyl)-2-(2-cyanoethyl)alanine methyl ester | Melting point: 104–106° C. |
| N—(4-Chloro-2-hydroxybenzoyl)-2-(2-cyanoethyl)alanine methyl ester | Melting point: 118–119° C. |
| N—(3-Fluoro-4-methylbenzoyl)-2-(2-cyanoethyl)alanine methyl ester | Melting point: 118–119° C. |
| N—(2-Mercaptobenzoyl)-2-(2-cyanoethyl)alanine methyl ester | Melting point: 90–93° C. |
| N—(2-Amino-4-chlorobenzoyl)-2-(2-cyanoethyl)alanine methyl ester | Melting point: 115–116° C. |
| N—(4-Chloro-3-nitrobenzoyl)-2-(2-cyanoethyl)alanine methyl ester | $n_D^{24} = 1.5575$ |
| N—(p-Chlorobenzoyl)-2-(2-cyanoethyl)methionine methyl ester | Melting point: 79–80° C. |
| N—(p-Chlorobenzoyl)-2-(2-cyanoethyl)phenylalanine methyl ester | $n_D^{25} = 1.5630$ |

EXAMPLE 6

(a) Disodium 2-(p-chlorobenzoylamino)-2-(2-cyanoethyl)malonate dihydrate and (b) 2-(p-chlorobenzoylamino)-2-(2-cyanoethyl)malonic acid A 1N solution of sodium hydroxide (80 ml) was added dropwise to a solution of 7.3 g of diethyl N-(p-chlorobenzoyl)-2-(2-cyanoethyl)aminomalonate in methanol (60 ml) at 0°–5° C., and the resulting mixture was stirred at room temperature for 16 hours. The reaction mixture was then concentrated under reduced pressure to a volume of 80 ml, and 60 ml of ethanol were added to the concentrate. The precipitate was filtered off, washed with 50 ml of ethanol and dried for 16 hours in vacuo, to afford 6.0 g of the desired disodium salt (a) as a colourless powder melting at 254°–255° C. (with decomposition).

Elementary analysis: Calculated for $C_{13}H_9N_2O_5Cl\cdot Na_2\cdot 2H_2O$: C, 39.97; H, 3.35; N, 7.19; Cl, 9.07%; Found: C, 40.43; H, 3.43; N, 7.14; Cl, 9.21%

Fifty milliliters of ethyl acetate were added to a solution of 4.0 g of disodium 2-(p-chlorobenzoylamino)-2-(2-cyanoethyl)malonate dihydrate in water (50 ml), and the resulting solution was adjusted to pH 2.0 by adding 1N hydrochloric acid at 0°–5° C. The organic layer was separated off and dried over magnesium sulphate. The solvent was distilled off and the resulting residue was recrystallized from diethyl ether, to give 3.2 g of the desired acid (b) as a colourless powder melting at 103°–105° C. (with decomposition).

Elementary analysis: Calculated for $C_{13}H_{11}N_2O_5Cl$: C, 50.26; H, 3.57; N, 9.02; Cl, 11.41%; Found: C, 49.84; H, 3.64; N, 9.03; Cl, 11.68%

The following compounds were obtained by using the method of the preceding Example:

| | |
|---|---|
| Disodium 2-(o-chlorobenzoylamino)-2-(2-cyanoethyl)malonate monohydrate | Melting point: 261–262° C. (with decomposition) |
| Disodium 2-(p-methylbenzoylamino)-2-(2-cyanoethyl)malonate monohydrate | Melting point: 263–264° C. (with decomposition) |
| 2-(o-Chlorobenzoylamino)-2-(2-cyanoethyl)malonic acid | Melting point: 108–111° C. (with decomposition) |

EXAMPLE 7

Injectable solution 10 mg of disodium 2-(p-chlorobenzoylamino)-2-(2-cyanoethyl)malonate dihydrate was dissolved in 5 ml of physiological saline. The resulting solution was sterilized by heating to give an injectable solution.

EXAMPLE 8

Injectable solution 10 mg of N-(p-chlorobenzoyl)-2-(2-cyanoethyl)alanine methyl ester were dissolved in 0.3 ml of N,N-dimethylacetamide, and 4.7 ml of physiological saline were added to the solution. The resulting solution was sterilized by heating to give an injectable solution.

EXAMPLE 9

| Capsules for oral administration | |
|---|---|
| N—(p-Chlorobenzoyl)-2-(2-cyanoethyl)alanine methyl ester | 50 mg |
| lactose | 100 mg |
| corn starch | 148.5 mg |
| magnesium stearate | 1.5 mg |
| total: | 300 mg |

The above ingredients, in powder form, were mixed and passed through a 30 mesh screen. 300 mg of the powder were placed in a No. 3 gelatin capsule to give a capsule preparation.

EXAMPLE 10

| Capsules for oral administration | |
|---|---|
| disodium 2-(p-chlorobenzoylamino)-2-(2-cyanoethyl)malonate dihydrate | 50 mg |
| lactose | 100 mg |
| corn starch | 148.5 mg |
| magnesium stearate | 1.5 mg |

| Capsules for oral administration | |
|---|---|
| Total: | 300 mg |

The above ingredients, in powder form, were mixed and passed through a 30 mesh screen. 300 mg of the powder were placed in a No. 3 gelatin capsule to give a capsule preparation.

PREPARATION 2-(p-Chlorophenyl)-4-(2-cyanoethyl)-4-methyl-5-oxazolone 2.8 g of N-(p-chlorobenzoyl)-2-(2-cyanoethyl)alanine and 2.0 g of acetic anhydride were dissolved in 30 ml of benzene and the solution was refluxed for one hour. The solvent was then distilled off and the resulting residue was recrystallized from di-isopropyl ether, to afford 2.1 g of the desired product as a colourless powder melting at 97°–98° C.

Elementary analysis: Calculated for $C_{13}H_{11}O_2N_2Cl$: C, 59.44; H, 4.22; N, 10.66; Cl, 13.50%; Found: C, 59.58; H, 4.24; N, 10.70; Cl, 13.40%

EXAMPLE 11

Stereospecific synthesis of N-(p-Chlorobenzoyl)-2-(2-cyanoethyl)alanine methyl ester (a)
N-(N-benzyloxycarbonyl-L-prolyl)-2-(2-cyanoethyl)alanine methyl ester—isomers (i) and (ii)

To a solution of crude N-benzyloxycarbonyl-L-prolyl chloride in dichloromethane (100 ml), obtained from N-benzyloxycarbonyl-L-proline (10.0 g) and phosphorus pentachloride (8.4 g), were added, at 5° C., 2-(2-cyanoethyl)alanine methyl ester (6.2 g) and triethylamine (5.6 ml), and the resulting mixture was stirred at 0°–5° C. for one hour. The reaction mixture was then washed with water (100 ml), and the organic layer was separated off and dried over magnesium sulphate. The solvent was distilled off and the residue was purified by silica gel Lobar column chromatography (flow rate 24 ml/minute; eluent: cyclohexane/ethyl acetate/triethylamine, 10/10/1) to isolate the two diastereoisomers. The two isomers were separately recrystallised from diethyl ether, giving 3.8 g and 4.1 g, respectively, in the form of colourless powders.

Isomer (i): Melting point: 98°–99° C.; $[\alpha]_D^{25} - 67.1°$ (C=1, MeOH)

Elementary analysis: Calculated for $C_{20}H_{25}N_3O_5$: C, 62.00; H, 6.50, N, 10.85%; Found: C, 62.12; H, 6.47; N, 10.89%

Isomer (ii): Melting point: 108°–109° C; $[\alpha]_D^{25} - 36.6°$ (C=1, MeOH)

Elementary analysis: Found: C, 62.14; H, 6.47; N, 10.88%

(b) 2-(2-cyanoethyl)alanine methyl ester—isomers (i) and (ii)

To a solution of isomer (i) of N-(N-benzyloxycarbonyl-L-prolyl)-2-(2-cyanoethyl)alanine methyl ester (3.0 g) in dichloromethane (30 ml) was added 1.7 g of phosphorus pentachloride, and the resulting mixture was refluxed for 30 minutes. The solvent was distilled off under reduced pressure and the residue was dissolved in dichloromethane (40 ml). The solution was cooled to −40° C. in a cooling bath, and propanol (5 ml) and triethylamine (10 ml) were added. The cooling bath was removed and the mixture was stirred for 30 minutes, then for another 1.5 hours at room temperature. The solvent was distilled off under reduced pressure and the residue was dissolved in methanol (30 ml). The methanol solution was cooled to 5° C., 30 ml of 0.5 N hydrochloric acid were added, and the mixture was stirred for 1.5 hours at room temperature. Water (50 ml) was added and the mixture was then washed with diethyl ether (100 ml). The aqueous layer was adjusted to about pH 8 with sodium bicarbonate solution and extracted with dichloromethane (100 ml×3). The combined organic extracts were dried over magnesium sulphate and the solvent was distilled off. The residue was purified by silica gel column chromatography, eluted with ethyl acetate, to give 0.91 g of isomer (i) of the desired product as a pale yellow liquid.

The above procedure was repeated, but using 3.0 g of isomer (ii) of the starting material, to give 0.93 g of isomer (ii) of the desired product as a pale yellow liquid.

Isomer (i): $n_D^{25} 1.4485$; $[\alpha]_D^{25} + 19.2°$ (C=1, MeOH)

Elementary analysis: Calculated for $C_7H_{12}N_2O_2$: C, 53.83; H, 7.74; N, 17.94%; Found: C, 53.85; H, 7.86; N, 18.10%

Isomer (ii): $n_D^{25} 1.4527$; $[\alpha]_D^{25} - 19.6°$ (C=1, MeOH)

Elementary analysis: Found: C, 54.17; H, 7.94; N, 17.65%

(c) N-(p-Chlorobenzoyl)-2-(2-cyanoethyl)alanine methyl ester—isomers (i) and (ii)

p-Chlorobenzoyl chloride (0.91 g) and triethylamine (0.91 ml) were added at 5° C. to a solution of 0.85 g of isomer (i) of the 2-(2-cyanoethyl)alanine methyl ester in dichloromethane (20 ml), and the resulting mixture was stirred at 0°–5° C. for 2 hours. The reaction mixture was then washed with water (20 ml) and the organic layer was dried over magnesium sulphate. The solvent was distilled off and the residue was purified by silica gel Lobar column chromatography (eluent: 1/1 cyclohexane/ethyl acetate; flow rate: 12 ml/minute), giving 1.13 g of isomer (i) of the desired product as a colourless powder.

The above procedure was repeated, but using 0.85 g of isomer (ii) of the starting material, giving 1.10 g of isomer (ii) of the desired product as a colourless powder.

Isomer (i): Melting point: 61°–62° C.; $[\alpha]_D^{25} - 19.0°$ (C=1, MeOH)

Elementary analysis: Calculated for $C_{14}H_{15}N_2O_3Cl$: C, 57.05; H, 5.13; N, 9.50; Cl, 12.03%; Found: C, 57.48; H, 5.34; N, 9.45; Cl, 12.02%

Isomer (ii): Melting point: 64°–65° C.; $[\alpha]_D^{25} + 19.9°$ (C=1, MeOH)

Elementary analysis: Found: C, 57.20; H, 5.03; N, 9.38; Cl, 11.90%

We claim:

1. Compounds having the formula

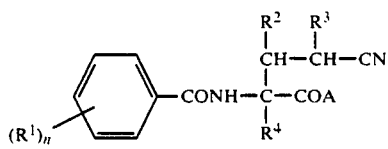

wherein
$R^1$ is a halogen atom;

$R^2$ and $R^3$ are both hydrogen atoms;
$R^4$ is an alkyl group having from 1 to 4 carbon atoms;
A is a hydroxy group or an alkoxy group having from 1 to 4 carbon atoms; and
n is 1;
and, when A is the hydroxy group, the pharmaceutically acceptable carboxylic acid salts thereof.

2. Compounds as claimed in claim 1, wherein:
$R^1$ is a chlorine atom;
$R^2$ and $R^3$ are both hydrogen atoms;
$R^4$ is a methyl group;
A is a hydroxy group or an alkoxy group having from 1 to 4 carbon atoms; and
n is 1;
and the sodium, potassium and calcium salts thereof.

3. Compounds as claimed in claim 1, selected from the group consisting of:
N-(p-Chlorobenzoyl)-2-(2-cyanoethyl)alanine methyl ester;
N-(p-chlorobenzoyl)-2-(2-cyanoethyl)alanine;
N-(p-Chlorobenzoyl)-2-(2-cyanoethyl)leucine methyl ester;
N-(m-Chlorobenzoyl)-2-(2-cyanoethyl)alanine methyl ester;
N-(m-Chlorobenzoyl)-2-(2-cyanoethyl)alanine;
N-(o-Chlorobenzoyl)-2-(2-cyanoethyl)alanine methyl ester;
N-(o-Chlorobenzoyl)-2-(2-cyanoethyl)alanine;
2-(2-Cyanoethyl)-N-(p-fluorobenzoyl)alanine methyl ester;
2-(2-Cyanoethyl)-N-(p-fluorobenzoyl)alanine;
2-(2-Cyanoethyl)-N-(p-bromobenzoyl)alanine methyl ester;
2-(2-Cyanoethyl)-N-(p-bromobenzoyl)alanine;
2-(2-Cyanoethyl)-N-(p-iodobenzoyl)alanine methyl ester;
2-(2-Cyanoethyl)-N-(p-iodobenzoyl)alanine.

4. The compound of claim 1 which is N-(p-chlorobenzoyl)-2-(2-cyanoethyl)alanine.

5. The compound of claim 1 which is N-(p-chlorobenzoyl)-2-(2-cyanoethyl)alanine methyl ester.

6. The compound of claim 1 which is N-(o-chlorobenzoyl)-2-(2-cyanoethyl)alanine methyl ester.

7. The compound of claim 1 which is N-(p-chlorobenzoyl)-2-(2-cyanoethyl)leucine methyl ester.

8. The compound of claim 1 which is N-(m-chlorobenzoyl)-2-(2-cyanoethyl)alanine methyl ester.

9. The compound of claim 1 which is N-(m-chlorobenzoyl)-2-(2-cyanoethyl)alanine.

10. The compound of claim 1 which is N-(o-chlorobenzoyl)-2-(2-cyanoethyl)alanine.

11. The compound of claim 1 which is 2-(2-cyanoethyl)-N-(p-fluorobenzoyl)alanine methyl ester.

12. The compound of claim 1 which is 2-(2-cyanoethyl)-N-(p-fluorobenzoyl)alanine.

13. The compound of claim 1 which is 2-(2-cyanoethyl)-N-(p-bromobenzoyl)alanine methyl ester.

14. The compound of claim 1 which is 2-(2-cyanoethyl)-N-(p-bromobenzoyl)alanine.

15. The compound of claim 1 which is 2-(2-cyanoethyl)-N-(p-iodobenzoyl)alanine methyl ester.

16. The compound of claim 1 which is 2-(2-cyanoethyl)-N-(p-iodobenzoyl)alanine.

* * * * *